| (12) | United States Patent | (10) Patent No.: | US 7,393,856 B2 |
|---|---|---|---|
| | Bellinger-Kawahara et al. | (45) Date of Patent: | Jul. 1, 2008 |

(54) ANTI-VIRAL USES OF BORINIC ACID COMPLEXES

(75) Inventors: Carolyn Bellinger-Kawahara, Redwood City, CA (US); Kirk R. Maples, San Jose, CA (US); Jocob J. Plattner, Berkeley, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 85 days.

(21) Appl. No.: 11/152,959

(22) Filed: Jun. 14, 2005

(65) Prior Publication Data

US 2006/0019927 A1     Jan. 26, 2006

Related U.S. Application Data

(60) Provisional application No. 60/579,419, filed on Jun. 14, 2004.

(51) Int. Cl.
*A61K 31/435*     (2006.01)
(52) U.S. Cl. ....................................................... 514/277
(58) Field of Classification Search ................... 514/277
See application file for complete search history.

(56) References Cited

FOREIGN PATENT DOCUMENTS

| WO | WO 01/02424 A | 1/2001 |
|---|---|---|
| WO | WO 2004/056322 A | 7/2004 |

*Primary Examiner*—Sreeni Padmanabhan
*Assistant Examiner*—Renee Claytor
(74) *Attorney, Agent, or Firm*—Morgan, Lewis & Bockius LLP

(57) ABSTRACT

Compositions and methods of use of borinic acid complexes, especially hydroxyquinoline, imidazole and picolinic acid derivatives, as anti-viral agents as well as therapeutic agents for the treatment of diseases caused by viruses are described.

15 Claims, No Drawings

ANTI-VIRAL USES OF BORINIC ACID COMPLEXES

1 CROSS REFERENCE TO RELATED U.S. PATENT APPLICATIONS

This patent application claims the benefit under 35 U.S.C § 119(e) from provisional U.S. Patent Application Ser. No. 60/579,419, filed Jun. 14, 2004, which is incorporated herein by reference in its entirety and for all purposes.

2 BACKGROUND OF THE INVENTION

2.1 Field of the Invention

The present invention relates to the field of anti-viral borinic acid ester compounds and uses thereof as well as preparing and using these compounds, and pharmaceutical compositions thereof.

2.2 The Related Art

One hallmark of the modem era of medicine has been the decline in morbidity and mortality associated with bacterial and fungal infections. However, similar successes against various viral infections have not been matched.

Viruses are implicated in a variety of animal and human disease. Numerous approaches have been proposed to combat these pathogens which include, but are not limited to, herpesviruses 1 and 2 (HSV-1 and HSV-2), influenza viruses A, B and C (orthomyxoviruses), parainfluenza viruses 1-4, syncytial virus, Epstein Barr virus, rhinoviruses, human immunodeficiency viruses (HIV), polioviruses, coxsackie viruses, echoviruses, rubella virus, varicella-zoster virus, neurodermatrophic virus, variola virus, cytomegalovirus, hepatitis A, B and C viruses, papoviruses, rabies virus, yellow fever virus, dengue virus, West Nile virus and severe acute respiratory syndrome (SARS) virus. Table 1 illustrates various viruses and their associated human diseases.

One approach in the development of anti-viral compounds has been to identify compounds which interfere with the normal viral metabolism and replication in infected host cells. During the screening of new borinic ester compounds, we have found that certain of these compounds show anti-viral activity in cell culture assay systems.

TABLE 1

| Virus Category | Pertinent Human Diseases |
| --- | --- |
| | RNA Viruses |
| Picornaviridae | Polio |
| | Human hepatitis A |
| | Human rhinovirus |
| Togavindae and Flaviviridae | Rubella (German measles) |
| | Yellow fever |
| Coronavindae | Human respiratory coronavirus (HCY) |
| | Severe acute respiratory syndrome (SAM) |
| Rhabdovindae | Lyssavirus - Rabies |
| Paramyxoviridae | Paramyxovirus - Mumps |
| | Morbillvirus - Measles |
| | Pneumovirus - Respiratory syncytial virus |
| Orthomyxoviridae | Influenza |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovinis- Sandfly fever (SFN) |
| | Uukuvirus - Uukuniemi (UUK) |
| | Rift Valley Fever- (RVFN) |

TABLE 1-continued

| Virus Category | Pertinent Human Diseases |
| --- | --- |
| Arenaviridae | Junin - Argentine hemorrhagic fever |
| | Machupo - Bolivian hemorrhagic fever |
| | Lassa - Lassa fever |
| | LCM- aseptic lymphocyctic chodomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| | DNA Viruses |
| Papovaviridae | Pediatric viruses that reside in kidney |
| Adenoviridae | Human respiratory distress and some deep-seated eye infections |
| Paivoviddae | Human gastrointestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Variceila zoster virus (VZV) |
| | Epstein-Sam virus (EBV) |
| | Human herpes virus 6 (HHV6) |
| Poxyiridae | Orthopoxyirus is sub-genus for smallpox |
| Hepadnaviddae | Hepatitis B virus (HBV) |
| | Hepatitis C virus (HCY) |

Many existing compounds currently in use for treating viral diseases are subject to resistance mechanisms, are expensive to make, do not adequately treat patients or have adverse side effects. Therefore, there is a continuing need for new compounds which act to kill viruses, to inhibit viral replication or to block the pathogenic action of viruses.

Thus, there continues to be a need in the medical arts for novel, more effective, anti-viral compounds, especially for treating infections that are either intrinsically poorly responsive or resistant to currently available therapies.

3 SUMMARY OF THE INVENTION

In one aspect, the present invention describes anti-viral borinic acid ester compounds. The compounds are borinate derivatives, especially borinic acid complexes, and include such compounds as derivatives of hydroxyquinolines, picolinic acids and imidazoles, useful as anti-viral agents.

The anti-viral boron compounds useful in the methods of the invention are also provided as pharmaceutical compositions that can be administered to an animal, most preferably a human, for treatment of a disease having viral etiology, or an opportunistic infection with a virus, in an animal, most preferably a human, such as a patient in an immunologically compromised or debilitated state of health. In preferred embodiments, the anti-viral borinic acid ester compounds useful in the methods and compositions of the present invention have the structures given by Formulas 1 or 2, with preferred substituents as disclosed herein.

The invention also provides methods for preparing the anti-viral compounds and pharmaceutical compositions thereof, and methods of using said compounds therapeutically. Kits and packaged embodiments of the compounds and pharmaceutical compositions for the treatment of viral infections are also contemplated.

The invention also relates to methods of treating viral infections, preferably herpesviruses 1 and 2 (HSV-1 and HSV-2), influenza viruses A, B and C, parainfluenza viruses 1-4, syncytial virus, Epstein-Barr virus, rhinoviruses, human immunodeficiency viruses (HIV), polioviruses, coxsackie viruses, echoviruses, rubella virus, varicella-zoster virus, neuroderma-tropic virus, variola virus, cytomegalovirus, hepatitis A, B and C viruses, papoviruses, rabies virus, yellow fever virus, dengue virus, West Nile virus and Severe Acute Respiratory Syndrome (SARS) virus, using the compounds disclosed herein.

4 DESCRIPTION OF SOME EMBODIMENTS OF THE INVENTION

This invention provides anti-viral agents and methods of use of anti-viral boron compounds, for treating and/or preventing infections caused by viruses.

The borinic acid ester compounds useful in the methods and compositions of the present invention have the structural Formulas 1 and 2:

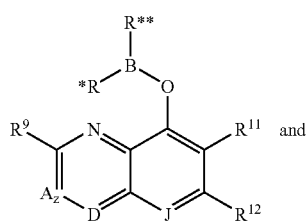

Formula 1

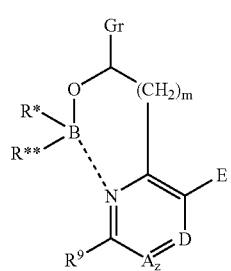

Formula 2 wherein: B is boron, O is oxygen;

wherein R* and R** are each independently selected from optionally substituted alkyl ($C_1$-$C_6$), optionally substituted cycloalkyl ($C_3$-$C_7$), optionally substituted alkenyl, optionally substituted alkynyl, aralkyl, optionally substituted aryl, optionally substituted heteroaryl, and optionally substituted heterocyclic;

and wherein z is zero or one and when z is 1, A is CH, $CR^{10}$ or N;

and wherein D is N, CH, or $CR^{14}$;

and wherein E is hydrogen, —OH, alkoxy, 2-(morpholinyl) ethoxy, —$CO_2H$, —$CO_2$alkyl, alkyl, $(CH_2)_nOH$ (n=1 to 3), —$CH_2NH_2$, —$CH_2NH$alkyl, —$CH_2N$(alkyl)$_2$, halogen, —CHO, —CH═NOH, —$NH_2$, or —$CF_3$;

and wherein m is zero to two;

and wherein r is 1 or 2, and wherein when r is 1, G is ═O (double-bonded oxygen) and when r is 2, each G is independently H, methyl, ethyl or propyl;

wherein $R^{14}$ is selected from —$(CH_2)_kOH$ (where k=1, 2 or 3), —$CH_2NH_2$, —$CH_2NH$-alkyl, —$CH_2N$(alkyl)$_2$, —$CO_2H$, —$CO_2$alkyl, —$CONH_2$, —OH, alkoxy, aryloxy, —SH, —S-alkyl, —S-aryl, —$SO_2$alkyl, —$SO_2N$(alkyl)$_2$, —$SO_2NH$alkyl, —$SO_2NH_2$, —$SO_3H$, —$SCF_3$, —CN, halogen, —$CF_3$, —$NO_2$, amino, substituted amino, —$NHSO_2$alkyl and —$CONH_2$;

and wherein J is $CR^{10}$ or N;

and wherein $R^9$, $R^{10}$, $R^{11}$ and $R^{12}$ are each independently selected from the group consisting of hydrogen, alkyl, —$(CH_2)_nOH$ (n=1 to 3), —$CH_2NH_2$, —$CH_2NH$alkyl, —$CH_2N$(alkyl)$_2$, halogen, —CHO, —CH═NOH, —$CO_2H$, —$CO_2$-alkyl, —S-alkyl, —$SO_2$-alkyl, —S-aryl, amino, alkoxy, —$CF_3$, —$SCF_3$, —$NO_2$, —$SO_3H$ and —OH;

including salts thereof, especially all pharmaceutically acceptable salts, hydrates, or solvates.

In a preferred embodiment of either of Formulas 1 or 2, R* and/or R** are the same or are different and one of R* and R** is an optionally substituted ($C_1$-$C_6$) or R* and R** are each an optionally substituted alkyl ($C_1$-$C_6$).

In a preferred embodiment of either of Formulas 1 or 2, R* and/or R** are the same or are different and one of R* and R** is an optionally substituted cycloalkyl ($C_3$-$C_7$) or R* and R** are each an optionally substituted cycloalkyl ($C_3$-$C_7$).

In a preferred embodiment of either of Formulas 1 or 2, R* and/or R** are the same or are different and one of R* and R** is an optionally substituted alkenyl or R* and R** are each an optionally substituted alkenyl. In a further preferred embodiment thereof, the alkenyl is an optionally substituted vinyl having the following structure:

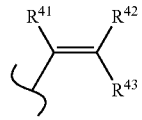

wherein $R^{41}$, $R^{42}$, and $R^{43}$ are each independently selected from the group consisting of hydrogen, alkyl, aryl, cycloalkyl, substituted aryl, aralkyl, —$(CH_2)_kOH$ (where k=1, 2 or 3), —$CH_2NH_2$, —$CH_2NH$alkyl, —$CH_2N$(alkyl)$_2$, —$CO_2H$, —$CO_2$alkyl, —$CONH_2$, —S-alkyl, —S-aryl, —$SO_2$alkyl, —$SO_2N$(alkyl)$_2$, —$SO_2NH$alkyl, —$SO_2NH_2$, —$SO_3H$, —$SCF_3$, —CN, halogen, —$CF_3$ and —$NO_2$.

In a preferred embodiment, the methods of the invention utilize compounds of Formulas 1 or 2 wherein R* and R** are the same or are different and wherein one of R* and R** is an optionally substituted alkynyl or R* and R** are each an optionally substituted alkynyl. In a further preferred embodiment thereof, the alkynyl has the following structure:

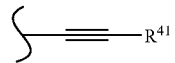

wherein $R^{41}$ is previously defined.

In a preferred embodiment of either of Formulas 1 or 2, R* and/or R** are the same or are different and one of R* and R** is an optionally substituted aryl or R* and R** are each an optionally substituted aryl. In a further preferred embodiment thereof the aryl is phenyl having the following structure:

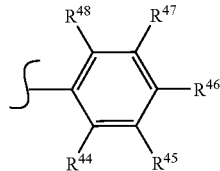

wherein $R^{44}$, $R^{45}$, $R^{46}$, $R^{47}$ and $R^{48}$ are each independently selected from the group consisting of alkyl, cycloalkyl, aryl, substituted aryl, aralkyl, —$(CH_2)_k$OH (where k=1, 2 or 3), —$CH_2NH_2$, —$CH_2$NH-alkyl, —$CH_2$N(alkyl)$_2$, —$CO_2$H, —$CO_2$alkyl, —$CONH_2$, —CONHalkyl, —CON(alkyl)$_2$, —OH, -alkoxy, -aryloxy, —SH, —S-alkyl, —S-aryl, —$SO_2$alkyl, —$SO_2$N(alkyl)$_2$, —$SO_2$NHalkyl, —$SO_2NH_2$, —$SO_3$H, —$SCF_3$, —CN, halogen, —$CF_3$, —$NO_2$, amino, substituted amino, —$NHSO_2$alkyl, —$OCH_2CH_2NH_2$, —$OCH_2CH_2$NHalkyl, —$OCH_2CH_2$N(alkyl)$_2$, oxazolidin-2-yl, or alkyl substituted oxazolidin-2-yl.

In a preferred embodiment the methods of the invention utilize compounds of Formulas 1 or 2 wherein R* and R** are the same or are different and wherein one of R* and R** is an optionally substituted benzyl or R* and R** are each an optionally substituted benzyl. In a further preferred embodiment thereof, the benzyl has the following structure:

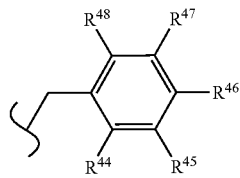

wherein $R^{44}$, $R^{45}$, $R^{46}$ $R^{47}$ and $R^{48}$ are previously defined.

In a preferred embodiment, the methods of the invention utilize compounds of Formula 1 wherein R* and R** are the same or are different and wherein one of R* and R** is an optionally substituted heteroaryl or R* and R** are each an optionally substituted heteroaryl. In a further preferred embodiment thereof, the heteroaryl has the follwoing structure:

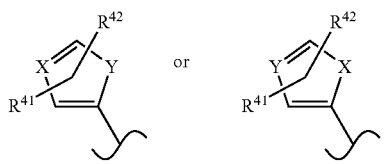

wherein X is CH=CH, N=CH, $NR^{50}$ (wherein $R^{50}$=H, alkyl, aryl or aralkyl), O, or S;

and wherein Y is CH or N when X is O, N or S;

and wherein $R^{41}$ and $R^{42}$ are as previously defined.

In another aspect, the present invention provides methods for treating viral disease in an animal, comprising administering to such animal an effective amount of a compound having the structure (Formula 3):

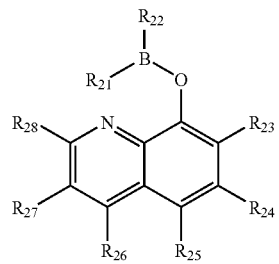

or it pharmaceutically acceptable salts, hydrates, or solvates: wherein B is boron and 0 is oxygen;

$R_{21}$ and $R_{22}$ are selected independently from the group consisting of optionally substituted alkenyl, optionally substituted cycloalkyl, optionally substituted aryl, optionally substituted heteroaryl, and optionally substituted heterocyclic.

$R_{23}$-$R_{28}$ are selected independently from the group consisting of hydrogen, alkyl, hydroxy, alkoxy, halo, cyano, aryl, aralkyl, heteroaralkyl, heteroaryl, aryloxy, heteroaryloxy, thio, alkylthio, arylthio, heteroarylthio, cycloalkyl, heterocyclyl, cycloalkyloxy, heterocyclyloxy, formyl, carboxy, thioformyl, thiocarboxy, sulfonyl, alkylsulfonyl, arylsulfonyl, heteroarylsulfonyl, alkylsulfinyl, arylsulfinyl, heteroarylsulfinyl, amino, alkylamino, dialkylamino, arylamino, diarylamino, alkylsulfonylamino, arylsulfonylamino; and wherein each of the above-recited alkyl-, aryl-, and heteroaryl-containing moieties is optionally substituted.

In some embodiments, $R_{21}$ is optionally substituted aryl or optionally substituted heteroaryl. In more specific embodiments, $R_{21}$ is optionally substituted aryl. Still more specific embodiments provide that $R_{21}$ is optionally substituted aryl and $R_{22}$ is optionally substituted aryl. In yet more specific embodiments, $R_{21}$ and $R_{22}$ independently are optionally substituted phenyl. More specific embodiments include those for which $R_{21}$ and $R_{22}$ independently are phenyl substituted with at least one moiety selected from the group consisting of: halo, hydroxy, thio, amino, formyl, thioformyl, carboxy, carbamoyl, thiocarbamoyl, cyano, optionally substituted alkoxy, alkylthio, aryloxy, arylthio, alkylamino, dialkylamino, arylamino, diarylamino, and alkylcarbonyloxy.

Of the latter embodiments, preferred compounds of Formula 3, include those wherein $R_{21}$ and $R_{22}$ independently are phenyl substituted with at least one moiety selected from the group consisting of: halo, hydroxy, thio, amino, formyl, thioformyl, carboxy, carbamoyl, thiocarbamoyl, cyano, optionally substituted alkoxy, alkylthio, aryloxy, arylthio, alkylamino, dialkylamino, arylamino, diarylamino, and alkylcarbonyloxy. Still more specific compounds include those where additionally $R_{23}$-$R_{28}$ are selected independently from the group consisting of: hydrogen, halo, hydroxy, thio, amino, formyl, thioformyl, carboxy, carbamoyl, thiocarbamoyl, cyano, optionally substituted alkoxy, alkylthio, aryloxy, arylthio, alkylamino, dialkylamino, arylamino, diarylamino, and alkylcarbonyloxy.

In other embodiments of Formula 3, $R_{21}$ and $R_{22}$ independently are phenyl substituted with at least one moiety selected from the group consisting of: halo, hydroxy, thio, amino, formyl, thioformyl, carboxy, carbamoyl, thiocarbamoyl, cyano, optionally substituted alkoxy, alkylthio, aryloxy, arylthio, alkylamino, dialkylamino, arylamino, diarylamino, and alkylcarbonyloxy, and $R_{23}$-$R_{28}$ independently are hydrogen, halo, or amino.

Other embodiments of the present invention include the use of compounds having the structure of Formula 3 in which $R_{23}$-$R_{28}$ independently are hydrogen, halo, or amino and $R_{21}$ and $R_{22}$ independently are phenyl substituted with at least one moiety selected from the group consisting of: halo, hydroxy, and amino. Particularly useful embodiments are those in which the compound is (3-fluorophenyl)(4-chlorophenyl) borinic acid 5,7-dichloro-8-hydroxyquinoline ester, bis(3-chlorophenyl)borinic acid 2-amino-8-hydroxyquinoline ester or (3-chlorophenyl)(3,4-dimethoxyphenyl)borinic acid 8-hydroxyquinoline ester.

In another aspect, the invention provides methods for a viral disease in an animal, comprising administering to such animal an effective amount of a compound having the structure (Formula 4):

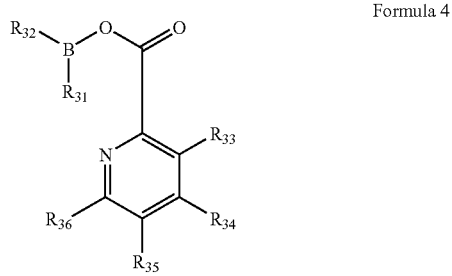

Formula 4 or its pharmaceutically acceptable salts, hydrates, or solvates; wherein B is boron and 0 is oxygen;

$R_{31}$ and $R_{32}$ are selected independently from the group consisting of optionally substituted alkyl, optionally substituted aryl, aralkyl, and optionally substituted heteroaryl.

$R_{33}$-$R_{36}$ are selected from the group consisting of: hydrogen, alkyl, aryl, arylcarbonyl, alkylcarbonyloxy, hydroxy, alkoxy, amino, dialkylamino, diarylamino, alkylamino, arylamino, carboxyalkyloxy, heterocyclyloxy, heterocyclyl, carboxy, hydroxyalkyl, aminoalkyl, (alkylamino)alkyl, (dialkylamino)alkyl, alkoxycarbonyl, carbamoyl, hydroxy, alkoxy, aryloxy, thio, alkylthio, arylthio, alkylsulfonyl, alkylsulfinyl, arylsulfinyl, dialkylsulfamoyl, alkylsulfamoyl, sulfamoyl, sulfonyl, cyano, halo, nitro, alkylcarbamoyl, wherein each of the above-recited moieties is optionally substituted. Optionally, $R_{35}$ and $R_{36}$ together with the ring atoms to which they are attached form an optionally substituted aromatic ring.

In some embodiments of the invention, the compounds of Formula 4 include those for which one of $R_{31}$ and $R_{32}$ is optionally substituted aryl. In more specific embodiments, the compounds of Formula 4 include those for which both $R_{31}$ and $R_{32}$ are optionally substituted aryl. Still more specific are those compounds of Formula 4 wherein both of $R_{31}$ and $R_{32}$ are optionally substituted phenyl. Yet more specific embodiments are those wherein both of $R_{31}$ and $R_{32}$ are optionally substituted phenyl and $R_{33}$-$R_{36}$ are selected independently from the group consisting of: hydrogen, hydroxy, alkoxy, amino, and carboxy. In still more specific embodiments in which both of $R_{31}$ and $R_{32}$ are optionally substituted phenyl and $R_{33}$-$R_{36}$ are selected independently from the group consisting of: hydrogen, hydroxy, alkoxy, amino, and carboxy. The optionally substituted phenyl is phenyl substituted by a moiety selected from the group consisting of: hydrogen, alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, -alkoxy, -aryloxy, —SH, —S-alkyl, —S-aryl, —S(O)alkyl, —S(O)aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl.

Among those compounds of Formula 4, preferred compounds include those where both of $R_{31}$ and $R_{32}$ are optionally substituted phenyl and $R_{33}$-$R_{36}$ are selected independently from the group consisting of: hydrogen, hydroxy, alkoxy, amino, or carboxy, the optionally substituted phenyl is phenyl substituted by a moiety selected from the group consisting of: hydrogen, alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —S(O)alkyl, —S(O)aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl. More specific embodiments include those in which at least one of $R_{33}$-$R_{36}$ is hydroxy or amino, and, still more specifically, where $R_{33}$ is hydroxy and $R_{34}$-$R_{36}$ are hydrogen. Of these latter compounds, more specific compounds include those for which the optionally substituted phenyl is phenyl substituted by a moiety selected from the group consisting of: hydrogen, halogen, and alkyl.

Other more specific compounds having the structure shown in Formula 4 are those for which $R_{33}$ is hydroxy and $R_{34}$-$R_{36}$ are hydrogen and both of $R_{31}$ and $R_{32}$ are optionally substituted phenyl where the optionally substituted phenyl is phenyl substituted by a moiety selected from the group consisting of: halogen, and alkyl and the halogen is chloro. More specific compounds are those in which $R_{33}$ is hydroxy and $R_{34}$-$R_{36}$ are hydrogen and both of $R_{31}$ and $R_{32}$ are optionally substituted phenyl where the optionally substituted phenyl is phenyl substituted by a moiety selected from the group consisting of: hydrogen, halogen, and alkyl and the halogen is chloro and the alkyl is methyl. Of these compounds, particularly useful is (bis(3-chloro-4-methylphenyl)boryloxy)(3-hydroxypyridin-2-yl)methanone, including its pharmaceutically acceptable salts, hydrates, or solvates.

In still other embodiments of the invention, the compounds shown in Formula 4 include those where both of $R_{31}$ and $R_{32}$ are optionally substituted phenyl and $R_{33}$-$R_{36}$ are selected independently from the group consisting of: hydrogen, hydroxy, alkoxy, amino, and carboxy. The optionally substituted phenyl is phenyl substituted by a moiety selected from the group consisting of: alkyl, cycloalkyl, aryl, substituted aryl, aralkyl, —(CH$_2$)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —S(O)alkyl, —S(O)aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl, and $R_{36}$ is amino, $R_{33}$ is hydroxy, and $R_{34}$ and $R_{35}$ are hydrogen. Of these compounds, useful compounds include those where the optionally substituted phenyl is phenyl substituted by a moiety selected from the group consisting of: hydrogen, halogen, and alkyl. More specific useful embodiments are those where the halogen is chloro. Of these compounds, the compound (bis(3-chlorophenyl)boryloxy)(6-amino-3-hydroxypyridin-2-yl)methanone, including its pharmaceutically acceptable salts, hydrates, and solvates, has useful properties.

In some embodiments, the compounds discussed hereinabove with respect to Formula 3 and Formula 4 are used to treat a viral disease associated with a virus selected from the group consisting of: picornaviridae, flaviviridae, coronaviridae, paramyxoviridae, orthomyxoviridae, retroviridae, herpesviridae and hepadnaviridae.

The structures of the invention also permit solvent interactions that may afford structures (such as Formulas 3 and 4) that include atoms derived from the solvent encountered by the compounds of the invention during synthetic procedures and therapeutic uses. Thus, such solvent structures can especially insinuate themselves into at least some of the compounds of the invention, especially between the boron and nitrogen atoms, to increase the ring size of such compounds by one or two atoms. For example, where the boron ring of a structure of the invention comprises 5 atoms, including, for example, the boron, a nitrogen, an oxygen and 2 carbons, insinuation of a solvent atom between the boron and nitrogen would afford a 6- or 7-membered ring. in one example, use of hydroxyl and amino solvents may afford structures containing an oxygen or nitrogen between the ring boron and nitrogen atoms to increase the size of the ring. Such structures are expressly contemplated by the present invention, preferably where R*** is H or alkyl.

Formula 5

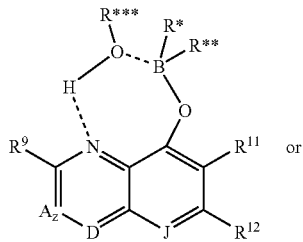

or

Formula 6

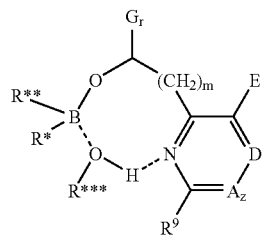

As used herein, the following terms have the stated meaning unless specifically defined otherwise in this application:

By "alkyl" in the present invention is meant straight or branched chain alkyl groups having 1-10 carbon atoms and preferably 1-6 carbon atoms. The terms "lower alkyl", and "$C_1$-$C_6$ alkyl" both refer to alkyl groups of 1-6 carbon atoms. Examples of such alkyl groups include, for instance, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "substituted alkyl" is meant an alkyl group having from 1 to 5 and preferably 1 to 3 and more preferably 1 substituent selected from alkoxy, substituted alkoxy, aryl, substituted aryl, aryloxy, substituted aryloxy, cycloalkyl, substituted cycloalkyl, heteroaryl, substituted heteroaryl, heterocyclic, substituted heterocyclic, hydroxyl, amino, substituted amino, carboxyl, -carboxyl-alkyl, amido, thiol, alkylthio, substituted alkylthio, arylthio, substituted arylthio, —$SO_2$-alkyl, —$SO_2$-amino, —$SO_2$-substituted amino, —$SO_2$—OH, —$SCF_3$, cyano, halo, nitro, and —$NHSO_2$alkyl.

By "substituted lower alkyl" is meant a lower alkyl group substituted with 1 to 5 and preferably 1 to 3 and more preferably 1 substituent as defined above for substituted alkyl.

By "alkylene" is meant a divalent alkyl group having from 1 to 10 carbon atoms, preferably from 1 to 5 carbon atoms and more preferably 1 to 3 carbon atoms. This term is exemplified by groups such as methylene, 1,2-ethylene, 1,3-n-propylene, 1,4-n-butylene, 2-methyl-1,4-propylene and the like.

By "substituted alkylene" is meant an alkylene group having from 1 to 5 and preferably 1 to 3 and more preferably 1 substituent as defined above for substituted alkyl.

By "alkoxy", "lower alkoxy", and "$C_1$-$C_6$ alkoxy" is meant straight or branched chain alkoxy groups having 1-6 carbon atoms, such as, for example, methoxy, ethoxy, propoxy, isopropoxy, n-butoxy, sec-butoxy, tent butoxy, pentoxy, 2-pentyl, isopentoxy, neopentoxy, hexoxy, 2-hexoxy, 3-hexoxy, and 3-methylpentoxy.

By "substituted alkoxy" is meant —O-substituted alkyl.

By "substituted lower alkoxy" is meant a —O-lower alkyl group substituted with 1 to 5 and preferably 1 to 3 and more preferably 1 substituent as defined above for substituted alkyl.

By "alkylcarbonyloxy" is meant —O—C(O)-alkyl.

By "hydroxyalkyl" is meant alkyl substituted with hydroxy.

By "hydroxyalkoxy" is meant alkoxy substituted with hydroxy.

By "carboxyalkyloxy" is meant —O-alkyl-COOH and salts thereof.

By "alkyloxycarbonyl" is meant —C(O)—O-alkyl.

By "alkenyl" in the present invention is meant an alkenyl group having from 2 to 6 carbon atoms and more preferably 2 to 4 carbon atoms and having at least 1 and preferably 1 site of alkenyl unsaturation. Examples of alkenyl groups include, for instance, vinyl, allyl, n-but-2-en-1-yl, and the like.

By "substituted alkenyl" is meant an alkenyl group having from 1 to 3 substituents and preferably one substituent selected from alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, alkylthio, substituted alkylthio, arylthio, substituted arylthio, —$SO_2$-alkyl, —$SO_2$-amino, —$SO_2$-substituted amino, —$SO_2$—OH, —$SCF_3$, cyano, halo, nitro, —$NHSO_2$alkyl, and —$C(O)SO_2$-alkyl with the proviso that any hydroxyl or thiol substitution is not on a vinyl carbon atom.

The terms alkenyl and substituted alkenyl encompass both the cis and trans isomers as well as mixtures thereof.

By "alkynyl" is meant an alkynyl group having from 2 to 6 carbon atoms and more preferably 2 to 4 carbon atoms and having at least 1 and preferably 1 site of alkynyl unsaturation. Examples of alkynyl groups include, for instance, acetylenyl, propargyl, n-but-2-yn-1-yl, and the like.

By "substituted alkynyl" is meant an alkynyl group having from 1 to 3 substituents and preferably one substituent selected from alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, alkylthio, substituted alkylthio, arylthio, substituted arylthio, —SO$_2$-alkyl, —SO$_2$-amino, —SO$_2$-substituted amino, —SO$_2$—OH, —SCF$_3$, cyano, halo, nitro, —NHSO$_2$alkyl, and —C(O)SO$_2$-alkyl with the proviso that any hydroxyl or thiol substitution is not on an acetylenic carbon atom.

By "amino" is meant —NH$_2$.

By "substituted amino" is meant as an —NR'R" group where R' and R" are independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic or where R' and R" and the nitrogen atom bound thereto form a heterocyclic or substituted heterocyclic group with the proviso that R' and R" and not both hydrogen.

By "alkylamino" is meant —NH-alkyl.

By "aminoalkyl" is meant -alkylene-NH$_2$.

By "dialkylamino" is meant —N(alkyl)(alkyl), where each alkyl may be the same or different.

By "(alkylamino)alkyl" is meant -alkylene-NH-alkyl, where each alkyl can be the same or different.

By "(dialkylamino)alkyl" is meant -alkylene-N(alkyl)(alkyl), where each alkyl can be the same or different.

By "arylamino" is meant —NH-aryl, where aryl is defined below.

By "alkylsulfonylamino" is meant —NH—SO$_2$alkyl.

By "arylsulfonylamino" is meant —NH—SO$_2$aryl, where aryl is defined below.

By "diarylamino" is meant —N(aryl)(aryl), where each aryl may be the same or different and aryl is defined below.

By "acyloxy" is meant the groups —OC(O)alkyl, —O(C) substituted alkyl, —OC(O)alkenyl, —OC(O)substituted alkenyl, —OC(O)alkynyl, —OC(O)substituted alkynyl, —OC(O)aryl, —OC(O)substituted aryl, —OC(O)cycloalkyl, —O(CO)substituted cycloalkyl, —OC(O)heteroaryl, —OC(O)substituted heteroaryl, —OC(O)heterocyclic, and —OC(O)substituted heterocyclic.

By "alkyloxycarbonyl" is meant —C(O)-Oalkyl.

By "amido" or "carbamoyl" is meant —C(O)amino and —C(O)substituted amino.

By "alkyl carbamoyl" is meant —C(O)—NH-alkyl.

By the term "halogen" or "halo" is meant fluorine, bromine, chlorine, and iodine.

By "cycloalkyl", e.g., C$_3$-C$_7$ cycloalkyl, is meant cycloalkyl groups having 3-7 atoms such as, for example cyclopropyl, cyclobutyl, cyclopentyl, cyclohexyl, and cycloheptyl.

By "substituted cycloalkyl" is meant a cycloalkyl group having from 1 to 3 and preferably one substituent selected from alkyl, substituted alkyl, alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, alkylthio, substituted alkylthio, arylthio, substituted arylthio, —SO$_2$-alkyl, —SO$_2$-amino, —SO$_2$-substituted amino, —SO$_2$—OH, —SCF$_3$, cyano, halo, nitro, —NHSO$_2$alkyl, —C(O)SO$_2$-alkyl, keto (C=O) and thioketo (C=S).

By the term "cycloalkyloxy" or "substituted cycloalkyloxy" is meant —O-cycloalkyl and —O-substituted cycloalkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), provided that the point of attachment is to an aromatic carbon atom.

By "substituted aryl" is meant an aryl group having from 1 to 3 and preferably one substituent selected from acyloxy, alkyl, substituted alkyl, alkoxy, substituted alkoxy, cycloalkyl, substituted cycloalkyl, aryl, substituted aryl, aryloxy, substituted aryloxy, heteroaryl, substituted heteroaryl, heterocyclic, substituted heterocyclic, hydroxyl, amino, substituted amino, carboxyl, -carboxyl-alkyl, amido, thiol, alkylthio, substituted alkylthio, arylthio, substituted arylthio, —SO$_2$-alkyl, —SO$_2$-amino, —SO$_2$-substituted amino, —SO$_2$—OH, —SCF$_3$, cyano, halo, nitro, —NHSO$_2$alkyl, and —C(O)SO$_2$-alkyl. In one embodiment, the substituted aryl group is mono-, di-, or tri-substituted with halo, lower alkyl, lower alkoxy, lower alkylthio, trifluoromethyl, lower acyloxy, aryl, heteroaryl, and hydroxy. Preferred aryl groups include phenyl and naphthyl, each of which is optionally substituted as defined herein.

By "aryloxy" is meant —O-aryl.

By "substituted aryloxy" is meant —O-substituted aryl.

By "arylcarbonyl" is meant —C(O)aryl.

By "aralkyl" is meant the groups -alkylene-aryl, -alkyene substituted aryl, -substituted alkylene-aryl and -substituted alkylene-substituted aryl.

By "carboxyl" or "carboxy" is meant —COOH and salts thereof.

"Alkanoyl" or "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "alkanoylamino" refers to the group —NH—C(O)H and —NHC(O)-alkyl, preferably the alkanoyl amino is —NHC(O)-alkyl.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, and benzoxazolyl. Preferred heteroaryls are thiazolyl, pyrimidinyl, preferably pyrimidin-2-yl, and pyridyl. Other preferred heteroaryl groups include 1-imidazolyl, 2-thienyl, 1-(or 2-)quinolinyl, 1-(or 2-) isoquinolinyl, 1-(or 2-)tetrahydroisoquinolinyl, 2-(or 3-)furanyl and 2-tetrahydrofuranyl.

By "substituted heteroaryl" is meant a heteroaryl group having from 1 to 3 and preferably one substituted as defined above for substituted aryl.

By "heteroaryloxy" and "substituted heteroaryloxy" is meant —O-heteroaryl and —O-substituted heteroaryl, respectively.

By "heteroaralkyl" is meant the groups -alkylene-heteroaryl, -alkylene substituted heteroaryl, -substituted alkylene-heteroaryl and -substituted alkylene-substituted heteroaryl.

By "heterocyclic" or "heterocycle" or "heterocyclyl" or "heterocycloalkyl" or "cycloheteroalkyl" is meant refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is to a heterocyclic ring atom.

By "substituted heterocyclic" is meant a heterocycle group that is substituted with from 1 to 3 and preferably 1 substituent of the same substituents as defined for substituted cycloalkyl.

By "heterocyclyloxy" is meant —O-heterocyclyl.
By "thiol" or "thio" is meant —SH.
By "alkylthio" is meant —S-alkyl.
By "substituted alkylthio" is meant —S-substituted alkyl.
By "arylthio" is meant —S-aryl.
By "substituted arylthio" is meant —S-substituted aryl.
By "heteroarylthio" is meant —S-heteroaryl.
By "cyano" is meand —CN.
By "formyl" is meant —C(=O)H or —CHO.
By "thioformyl" is meant —C(=S)H or —CHS.
By "sulfonyl" is meant —SO$_3$H.
By "alkylsulfonyl" is meant —SO$_2$alkyl.
By "arylsulfonyl" is meant —SO$_2$aryl.
By "heteroarylsulfonyl" is meant —SO$_2$heteroaryl.
By "alkylsulfinyl" is meant —SOalkyl.
By "arylsulfinyl" is meant —SOaryl.
By "heteroarylsulfinyl" is meant —SOheteroaryl.
By "sulfamoyl" is meant —SO$_2$—NH$_2$.
By "sulfamoyloxy" is meant —O—SO$_2$—NH$_2$.
By "alkylsulfamoyl" is meant —SO$_2$—NH-alkyl.
By "dialkylsulfamoyl" is meant —SO$_2$—N(alkyl)(alkyl), where each alkyl can be the same or different.

By "thiocarboxyl" is meant —C(=S)OH, —C(=O)SH, or —C(=S)SH.

By "thiocarbamoyl" is meant —C(=S)amino and —C(=S)substituted amino.

The term "aromatic ring" refers to optionally substituted aryl groups and optionally substituted heteroaryl groups.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl. Impermissible substitutions are not contemplated by the invention.

By "ligand" is meant a nitrogen-containing aromatic system that is capable of forming a dative bond with the Lewis acidic boron center, while appended as a borinate ester moiety. Such ligands are known to those trained in the arts. Examples are shown in the structures below

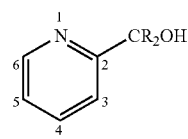

2-hydroxymethylpyridine R = H
2-(hydroxyisopropyl)pyridine R = Me

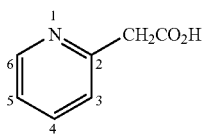

2-pyridylacetic acid

-continued

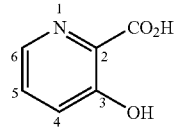

3-hydroxypicolinic acid

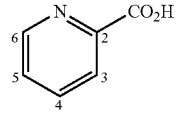

picolinic acid
(pyridine-2-carboxylic acid

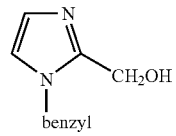

2-hydroxymethyl-
1H-benzylimidazole

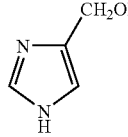

4-hydroxymethylimidazole

The compounds having the new discovered use have been implicated in the inhibition viral activity.

For oral administration, the compounds can be formulated readily by combining the active compounds with pharmaceutically acceptable carriers well known in the art. Such carriers enable the compounds of the invention to be formulated as tablets, pills, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin, for use in an inhaler can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g., polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethyl sulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitric, benzoic, citric, tartaric, maleic, hydroiodic, alkanoic such as acetic, HOOC—$(CH_2)r$—$CH_3$ where r is 0-4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the compounds can be formulated and administered through a variety of means, including systemic, localized, or topical administration.

For topical administration, the compounds can be formulated readily by combining the active compounds with pharmaceutically acceptable carriers well known in the art. Such carriers enable the compounds of the invention to be formulated as gels, slurries, suspensions, creams, and ointments for topical applications. if desired, disintegrating agents can be added, such as the cross-linked polyvinyl pyrrolidone, agar, or alginic acid or a salt thereof such as sodium alginate.

Techniques for formulation and administration can be found in *Remington's Pharmaceutical Sciences*, Mack Publishing Co., Easton, Pa., The mode of administration can be selected to maximize delivery to a desired target site in the body. Suitable routes of administration can, for example, include oral, rectal, transmucosal, transcutaneous, or intestinal administration. Parenteral delivery, including intramuscular, subcutaneous, and intramedullary injections, as well as intrathecal, direct intraventricular, intravenous, intraperitoneal, intranasal, or intraocular injections are also contemplated.

Alternatively, one can administer the compound in a local rather than systemic manner, for example, by injection of the compound directly into a specific tissue, often in a depot or sustained release formulation.

Pharmaceutical compositions suitable for use include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Preferred compounds for the invention anti-viral use will have certain pharmacological properties. Such properties include, but are not limited to, oral bioavailability, low toxicity, low serum protein binding and desirable in vitro and in vivo hall-lives. Assays may be used to predict these desirable pharmacological properties. Assays used to predict bioavailability include transport across human intestinal cell monolayers, including Caw-2 cell monolayers. Serum protein binding may be predicted from albumin binding assays. Such assays are described in a review by Oravcová, et al., (1996, *J. Chromat.* B 677: 1-27). Compound half-life is inversely proportional to the frequency of dosage of a compound. In vitro half-lives of compounds may be predicted from assays of microsomal half-life as described by Kuhnz and Gieschen (*Drug Metabolism and Disposition*, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl, et al, 1975, in *The Pharmacological Basis of Therapeutics*, Ch.1, p. 1).

Dosage amount and interval can be adjusted individually to provide plasma levels of the active moiety that are sufficient to maintain bacterial cell growth inhibitory effects. Usual patient dosages for systemic administration range from 100-2000 mg/day. Stated in terms of patient body surface areas, usual dosages range from 50-910 mg/m$^2$/day. Usual average plasma levels should be maintained within 0.1-1000 M. In cases of local administration or selective uptake, the effective local concentration of the compound cannot be related to plasma concentration.

This invention relates to composition and methods for the treatment of diseases of both animals and human caused by pathogenic viruses. The anti-viral compounds of the invention are useful for the treatment of diseases of both animals and humans, including but not limited to human hepatitis A-B, human rhinoviruses, Yellow fever, human respiratory coronaviruses, Severe acute respiratory syndrome (SARS), respiratory syncytial virus, influenza, human immunodeficiency virus 1 (HIV-1), human immunodeficiency virus 2 (HIV-2), Herpes simplex virus 1 (HSV-1), Herpes simplex virus 2 (HSV-2), human cytomegalovirus (HCMV), Varicella zoster virus, Epstein-Barr (EBV).

The disclosures in this application of all articles and references, including patents and patent applications, are incorporated herein by reference in their entirety.

The compounds of this invention comprise a novel class of anti-viral agents. Medically-important viral species that are susceptible to these agents include, but are not limited to picornaviridae, flaviviridae, coronaviridae, paramyxoviridae, orthomyxoviridae, retroviridae, herpesviridae and hepadnaviridae.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those skillful in the art will have sufficient knowledge of such systems and methodologies so as to be able, without undue experimentation, to make such substitutions as will optimally serve their purposes in using the methods and procedures disclosed herein.

5 EXAMPLES

The invention is described in more detail in the following non-limiting examples. It is to be understood that these methods and examples in no way limit the invention to the embodiments described herein and that other embodiments and uses will no doubt suggest themselves to those skilled in the art.

The compounds of this invention are evaluated for their anti-viral activity as per the guidelines and procedures prescribed.

5.1 Protocols for Anti-Viral Activity in Vitro:

5.1.1 Yellow Fever (YFV) Anti-Viral Assay

Yellow Fever (YFV) anti-viral assay was performed with HeLa cells which were used in order to allow for a 7-day assay endpoint. HeLa cells were passaged in T-75 flasks. On the day preceding the assay, the cells were trypsinized, pelleted, counted and resuspended at $1 \times 10^4$/well in tissue culture medium in 96-well flat bottom tissue culture plates in a volume of 100 pl per well. One day following plating of cells, the wells were washed and the medium was replaced with complete medium (2% serum) containing various concentrations of test compound diluted in medium in a half-log series. A pretitered aliquot of 17D strain YFV virus was removed from the freezer (−80° C.) just before each experiment. The virus was diluted into tissue culture medium such that the amount of virus added to each well would give complete cell killing at 7 days post-infection.

5.1.2 HepG2 2.15 Anti-viral Evaluation Assay

HepG2 2.2.15 cells, which produce HBV aywl strain, were plated in 96-well collagen coated microtiter plates at a density of $2.5 \times 10^4$/well with DMEM medium supplemented with 2% fetal bovine serum. One day following plating of cells, the wells were washed and the medium was replaced with complete medium containing the test compound diluted in the medium in a half-log series.

The medium was replaced once with the fresh medium containing the freshly diluted compound three days post the initial addition of the lamivudine, a positive control compound. Cell viability was determined using CellTiter 96® Reagent (Promega, Madison, Wis.) according to the manufacturer's protocol, using a Vmax plate reader (Molecular Devices, Sunnyvale, Calif.). The mixture is metabolized by the mitochondrial enzymes of metabolically active cells to a soluble formazan product, allowing the rapid quantitative analysis of cell numbers. The media was removed and replaced with 100 μL of fresh media and 10 μL of Cell Titer 96. Plates were reincubated for 4 hours at 37° C. and read spectrophotometrically at 490- and 650 nm with a Molecular Devices Vmax plate reader. Percent cell viability of compound treated wells compared to no compound controls was calculated using an in-house computer program which graphs the percent reduction in viral cytopathic effects and the cell numbers at each drug concentration relative to control values. The program interpolates the inhibitory concentration of drug that reduces cytopathic effects by 50% ($IC_{50}$) and the toxic concentration that kills 50% of cells ($TC_{50}$).

5.1.3 HCY RNA Replicon Anti-Viral Evaluation Protocol

E-I

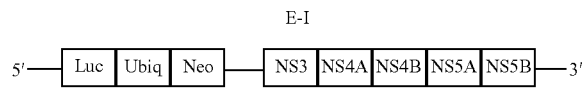

The cell line ET (luc-ubi-neo/ET), a new HCV RNA replicon that contains a stable luciferase (LUC) reporter, was used. The composition of the replicon is shown diagrammatically in FIG. 1 (ref, Krieger, N., V. Lohmann, and R. Bartenschlager. 2001. "Enhancement of hepatitis C virus RNA replicon replication by cell culture adaptive mutations." J. Virol. 75:4614-4624). The HCV RNA replicon ET contains the 5' NTR (IRES) of HCV (5') which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV non-structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The LUC reporter is used as an indirect measure of HCV replication. The activity of the LUC reporter is directly proportional to HCV RNA levels and positive control antiviral compounds behave comparably using either LUC or RNA endpoints. The use of the LUC endpoint is more economical than HCV RNA and can be used for high-throughput applications to screen libraries of compounds.

The HCV RNA replicon anti-viral evaluation assay examines the effects of compounds at five half-log concentrations each. Human interferon α2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hours later when the cells are still subconfluent. Compound $IC_{50}$ and $IC_{90}$ values are derived from HCV RNA levels assessed as either HCV RNA replicon-derived LUC activity or as HCV RNA using TaqMan RT-PCR. Compound $TC_{50}$ and TC90 values are calculated using a colorimetric assay as an indicator of cell numbers and cytotoxicity when the LUC assay system is employed, while ribosomal (rRNA) levels determined using TaqMan RTPCR are used as an indication of cell numbers in the RNA-based assay. Compound $TI_{50}$ and $TI_{90}$ values are calculated from spreadsheets.

5.2 Borinate Complexes

The above procedures were used to obtain the results in the following tables. Representative anti-viral data for the compounds 10 to 81 is shown in Table 1 as $IC_{50}$ (50% Inhibitory Concentration) with the values expressed as micrograms per ml. Thus, the invention provides anti-viral compounds that are generically called borinic acid complexes or esters, most preferably derived from disubstituted borinic acids.

The synthesis of the compounds of the invention is accomplished in several formats. Reaction scheme #1 demonstrate the synthesis of the intermediate borinic acids, and their subsequent conversion to the desired borinic acid complexes. When R* and R** are identical, the reaction of two equivalents of an aryl magnesium halide (or aryl lithium) with trialkyl borate, followed by acidic hydrolysis affords the desired borinic acid 5. When R* and R** are not identical, the reaction of an equivalent of an aryl magnesium halide (or aryl lithium) with appropriate aryl(dialkoxy)borane (4), heteroaryl(dialkoxy)borane or alkyl(dialkoxy)borane (alkoxy group comprised of methoxy, ethoxy, isopropoxy, or propoxy moiety), followed by acidic hydrolysis affords the unsymmetrical borinic acids 6 in excellent yields. Where applicable, the reaction of the alkylene esters (3, T=single bond, $CH_2$, $CMe_2$) with the appropriate organocerium, organolithium, organomagnesium or equivalent reactant is convenient.

As shown in Scheme 1, the borinic acid complexes are obtained from the precursor borinic acids by reaction with one equivalent of the desired heterocyclic ligand in suitable solvents (i.e., ethanol, isopropanol, dioxane, ether, toluene, dimethylformamide, N-methylpyrrolidone, or tetrahydrofuran).

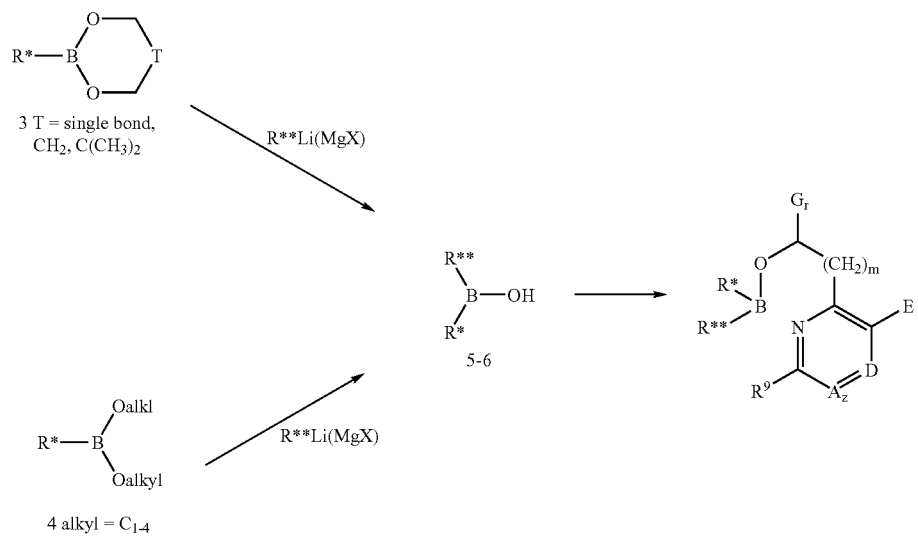

In certain situations, compounds of the invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention include, but are not limited to, the compounds disclosed herein and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. In a preferred embodiment, the compounds of the invention comprise any of compounds 13-15, and 81 (Tables 2 to 4), and variants thereof.

TABLE 2

In vitro Anti-viral Activity for HIV-1 and HIV-2

| Compound | Anti-HIV-1 Activity | | Anti-viral Index | Anti-HIV-2 Activity | | Anti-viral Index |
| | $IC_{50}$ (μM) | $TC_{50}$ (μM) | | $IC_{50}$ (μM) | $TC_{50}$ (μM) | |
| --- | --- | --- | --- | --- | --- | --- |
| 13 | 0.42 | 2.75 | 6.55 | 0.2 | 1.47 | 7.35 |
| 14 | 0.81 | 8.62 | 10.64 | | | |
| 15 | 0.17 | 2.50 | 14.71 | 0.04 | 0.53 | 13.3 |
| 80 | 2.53 | 15.20 | 6.01 | 2.35 | 7.42 | 3.17 |

TABLE 3

In vitro Anti-viral Activity for HSV-1 and HSV-2

| Compound | Anti-HSV-1 Activity | | Anti-viral Index | Anti-HSV-2 Activity | | Anti-viral Index |
| | $IC_{50}$ (μM) | $TC_{50}$ (μM) | | $IC_{50}$ (μM) | $TC_{50}$ (μM) | |
| --- | --- | --- | --- | --- | --- | --- |
| 13 | >32 | 10 | 0.312 | 3.52 | 9.76 | 2.80 |
| 14 | 7.85 | 17.6 | 2.24 | | | |
| 15 | 9.68 | >32 | >3.31 | >50 | 32.9 | <0.7 |
| 80 | 9.6 | >32 | 3.33 | 9.74 | 31.4 | 3.24 |
| Acyclovir | 17.98 μM | >100 | >5.56 | 7.61 | >100 | >13.2 |

TABLE 4

In vitro Anti-HBV Activity

| Compound | IC$_{50}$ (µg/ml) | TC$_{50}$ (µg/ml) | Anti-viral Selectivity Index |
|---|---|---|---|
| 80 | 2.51 | 3.10 | 1.24 |
| 81 | 6.2 | 6.50 | 1.05 |
| 13 | 0.44 | 2.10 | 4.78 |
| Lamivudine | 0.0093 µM | >1.0. µM | >1075 |

The present invention also encompasses the anti-viral use of the acylated prodrugs of the compounds. Those skilled in the art will recognize various synthetic methodologies which may be employed to prepare non-toxic pharmaceutically acceptable addition salts and acylated prodrugs compounds for the treatment of viral infections.

5.3 Synthetic Examples

5.3.1 General

Proton NMR are recorded on Varian AS 400 spectrometer and chemical shifts are reported as δ (ppm) down field from tetramethylsilane. Mass spectra are determined on Micromass Quattro II and Applied Biosystem AP3000. Compound identification numbers appear in parentheses and some of them correspond to the numbers in Scheme 1, Tables 1-3.

5.3.2 Formation of Ethylene Glycol Boronate Ester (3, T=single bond) General Procedure Boronic acid was dissolved in dry THF or dry diethyl ether (~10 mL/g) under nitrogen. Ethylene glycol (1 molar equivalent) was added to the reaction and the reaction was heated to reflux for 1- to 4 hours. Reaction was cooled to room temperature and solvent was removed under reduced pressure leaving the ethylene glycol ester as an oil or a solid. In cases where an oil was obtained or a solid that dissolved in hexane, dry hexane was added and removed under reduced pressure. The product was then placed under high vacuum for several hours. In cases where a solid was obtained that did not dissolve in hexane, the solid was collected by filtration and washed with cold hexane.

5.3.2.1 3-Cyanophenylboronic acid ethylene glycol ester (3a)

3-Cyanophenyl boronic acid (1 g, 6.8 mmol) was dissolved in dry THF (10 mL) under nitrogen. Ethylene glycol (379 µL, 422 mg, 6.8 mmol) was added and the reaction was heated to reflux for 4 hours then cooled to room temperature. THF was removed by rotary evaporator to give a white solid. Cold hexane was added and the product was collected by filtration giving a white solid (1.18 g, quant. yield). $^1$H-NMR (300.058 MHz, DMSO-d6) δ ppm 7.92-8.01 (3H, m), 7.50-7.64 (1H, m), 4.35 (4H, s)

5.3.2.2 Thiophene 3-boronic acid ethylene glycol ester (3b)

Thiophene-3-boronic acid (1 g, 7.8 mmol) was dissolved in dry THF (10 mL) under nitrogen. Ethylene glycol (435 µL, 484 mg, 7.8 mmol) was added and the reaction was heated to reflux for 1 hour then cooled to room temperature. THF was removed by rotary evaporator to give a white solid. Hexane was added, dissolving the solid and removed by rotary evaporation. The product was placed under high vacuum to yield a tan solid (1.17 g, 97%). $^1$H-NMR (300.058 MHz, CDCl3) δ ppm 7.93 (1H, s), 7.3-7.4 (2H, m), 4.35 (4H, s).

5.3.3 Formation of Unsymmetrical Borinic Acid (6) From Boronic Acid Ethylene Glycol Ester General Procedure A: Grignard Methodology Boronic acid ethylene glycol ester was dissolved in dry THF (10-20 mL/g) under nitrogen. Solution was cooled to −78° C. in an acetone-dry ice bath or to 0° C. in an ice-water bath. Grignard reagent (0.95 to 1.2 molar equivalent) was added drop wise to the cooled solution. The reaction was warmed to room temperature and stirred for 3-18 hours. 6N HCl (2 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or pyridine, then after stirring at room temperature for 3-18 hours, water (2 mL/g) was added and the pH adjusted to −8. Product was extracted into diethyl ether or ethylacetate or THF up to three times (40 mL/g). Organic layer was dried (MgSO$_4$), filtered and the solvent was removed by rotary evaporation giving the crude product, which is either purified by column chromatography or taken onto the next step without purification.

5.3.3.1 (4-Cyanophenyl)(3-fluorophenyl)borinic acid (6a)

4-Cyanophenyl boronic acid ethylene glycol ester (500 mg, 2.89 mmol) was dissolved in dry THF under nitrogen. The solution was cooled to −78° C. in an acetone/dry ice bath and 3-fluorophenylmagnesium bromide (1M in THF, 2.74 mL, 2.74 mmol, 0.95 molar equivalent) was added drop wise to the cold solution. The reaction was allowed to warm slowly to room temperature and stirred for 18 hours. 6N HCl (1 mL) was added to the reaction causing a cloudy appearance and the solvent was removed using a rotary evaporator. The product was extracted into diethyl ether (20 mL) and washed with water (3×20 mL). The organic layer was dried (MgSO$_4$), filtered and the solvent removed using a rotary evaporator to yield the crude product as an oily solid. This was taken onto the next step without purification.

5.3.4 General Procedure B: (Hetero)aryllithium methodology

The (hetero)aryl-bromide or iodide was dissolved in dry THF (20-30 mL/g) under nitrogen and degassed. The solution was cooled to −78° C. in an acetone-dry ice bath and n-, sec- or tert-butyllithium in THF or other solvent (1.2-2.4 molar equivalents) was added to the cooled solution drop wise generally causing the solution to turn deep yellow. The boronic acid ethylene glycol ester (1 molar equivalent) was dissolved in dry THF or diethyl ether (2-10 mL/g) under nitrogen. The boronic acid ethylene glycol ester in THF was added drop wise to the cooled aryl-lithium solution generally causing the solution to turn pale yellow. The reaction was warmed to room temperature and stirred for 1-18 hours. 6N HCl (2-4 mL/g) was added and solvent was removed under reduced vacuum. Product was extracted into diethyl ether (40 mL/g) and washed with water (3×equal volume). Organic layer was dried (MgSO$_4$), filtered and the solvent was removed by rotary evaporation giving the crude product, which is either purified by column chromatography or taken onto the next step without purification. Alternative work-up: if the borinic acid product contained a basic group such as an amine or

5.3.4.1 (3-Thienyl)(3-chlorophenyl)borinic acid (6b)

3-Chloro-bromobenzene (447 μL, 728 mg, 3.8 mmol) was dissolved in dry THF (15 mL) under nitrogen. The solution was degassed and cooled to −78° C. in an acetone-dry ice bath. tert-Butyllithium (1.7M in THF, 4.47 mL, 7.6 mmol, 2 molar equivalent) was added to the cooled solution drop wise causing the solution to turn deep yellow. The solution was stirred at −78° C. while 3-thiopheneboronic acid ethylene glycol ester (586 mg) was dissolved in dry diethyl ether (1 mL). The boronic ester solution was then added drop wise to the cooled solution causing the color to change to pale yellow. The reaction was warmed to room temperature and stirred for 18 hours. 6N HCl (2 mL) was added and the reaction was stirred for 1 hour. The solvent was removed using a rotary evaporator. The product was extracted into diethyl ether (10 mL) and washed with water (2×10 mL). The organic layer was dried (MgSO$_4$), filtered and the solvent removed using a rotary evaporator to yield the crude product as an orange oil. The product was purified by column chromatography using silica gel and hexane:ethyl acetate 5:1 as eluent giving the pure product as a clear oil (614 mg, 73%).

5.3.4.2 (3-Chlorophenyl)vinylborinic acid (6c)

This was prepared by a similar process as described for 6b by the reaction of 3-cyanophenyl boronic acid ethylene glycol ester with vinylmagnesium bromide.

5.3.4.3 (3-Fluoro-5-chlorophenyl)ethynylborinic acid (6d)

This was prepared by a similar process as described for 6b by the reaction of 3-fluoro-5-chlorophenyl boronic acid ethylene glycol ester with ethynylmagnesium bromide.

5.3.4.4 (4-Methyl-3-chlorophenyl)(2-thienyl)borinic acid (6e)

This was prepared by a similar process as described for 6b by the reaction of 2-thienylboronic acid ethylene glycol ester with 4-methyl-3-chlorophenyltithium.

5.3.4.5 (4-Cyanophenyl)ethynylborinic acid (6f)

This was prepared by a similar process as described for 6b by the reaction of 4-cyanophenylboronic acid ethylene glycol ester with ethynylmagnesium bromide.

5.3.4.6 (3-Fluorophenyl)Cyclopropylborinic acid (6g)

This was prepared by a similar process as described for 6b by the reaction of 3-fluorophenylboronic acid ethylene glycol ester with cyclopropyllithium.

5.3.4.7 (3-Thienyl)methylborinic acid (6h)

This was prepared by a similar process as described for 6b by the reaction of 3-thienylboronic acid ethylene glycol ester with methyllithium.

5.3.4.8 (4-Pyridyl)phenylborinic acid (6i)

This was prepared by a similar process as described for 6b by the reaction of phenylboronic acid ethylene glycol ester with 4-pyridyllithium.

5.3.4.9 (3-Cyanophenyl)(2-fluorophenyl)borinic acid (6j)

This was prepared by a similar process as described for 6b by the reaction of 3-cyanophenylboronic acid ethylene glycol ester with 2-fluorophenyllithium.

5.3.5 Formation of Symmetrical Borinic Acid (5) By Reaction of Organometallics With Trialkyl Borates: Bis(4-Chlorophenyl)Borinic Acid (5a) (Procedure C)

A cold solution (−78° C.) of trimethyl borate (0.37 mL) in dry tetrahydrofuran (THF, 25 mL) was treated drop wise with 4-chlorophenylmagnesium bromide (6.75 mL, 1M solution in ether). The reaction mixture was stirred at −78° C. for 1 h and then stirred for 18 h at room temperature. The solvent was removed under reduced pressure. The resultant residue was stirred with 100 mL of ether and 15 mL of 6N hydrochloric acid. Organic layer was separated and aqueous layer was extracted with ether (2×100 mL). The combined organic extract was washed with brine and dried over anhydrous magnesium sulfate. Solvent was removed to give light yellowish solid. The product was chromatographed over silica gel (Hex: Ether=1:1) to give 420 mg of borinic acid. $^1$H NMR (400 MHz, CDCl3) δ: 5.84 (s, OH), 7.46 (d, 4H, Ar—H), 7.72 (d, 4H, Ar—H).

5.3.5.1 Bis(3-chloro-4-methylphenyl)borinic acid (5b)

In a similar manner as for 5a, the titled compound was obtained from the reaction of 3-chloro-4-methylphenylmagnesium bromide with trimethyl borate. The product was obtained by chromatography over silica gel.

5.3.5.2 Bis(3-fluoro-4-methylphenyl)borinic acid (5c)

In a similar manner as for 5a, the titled compound was obtained from the reaction of 3-fluoro-4-methylphenyllithium with trimethyl borate. The product was obtained by chromatography over silica gel.

5.3.5.3 Bis(3-chloro-4-methoxyphenyl)borinic acid (5d)

In a similar manner as for 5a, the titled compound was obtained from the reaction of 3-chloro-4-methoxyphenyllithium with trimethyl borate. The product was obtained by chromatography over silica gel.

5.3.5.4 Bis(3-fluoro-4-methoxyphenyl)borinic acid (5e)

In a similar manner as for 5a, the titled compound was obtained from the reaction of 3-fluoro-4-methoxyphenyllithium with trimethyl borate. The product was obtained by chromatography over silica gel.

5.3.6 Formation of unsymmetrical borinic acids (6) by reaction of organometallics with alkyl(aryl)dialkoxyboranes. (4-Chlorophenyl)methylborinic acid (6k) (Procedure D)

To 4-chlorophenylmagnesium bromide (5.5 mL, 1M solution in ether) at −78° C., di(isopropoxy)methylborane (1 mL, 0.78 g) was added drop wise via syringe. The reaction mixture was stirred at −78° C. for 1 h and then stirred overnight at ambient temperature. The reaction mixture was treated drop wise with 100 mL of ether and 15 mL of 6N hydrochloric acid, and stirred for 1 h. Organic layer was separated and aqueous layer was extracted with ether (2×100 mL). The combined organic extract was washed with brine and dried over anhydrous sodium sulfate. Solvent was removed under reduce pressure to give 1.1 g of oil. $^1$H NMR of the product was consistent for (4-chlorophenyl)methyl borinic acid.

5.3.6.1 (4-Fluorophenyl)methylborinic acid (6m)

In a similar manner as for 6k, the titled compound was obtained from the reaction of 4-fluorophenylmagnesium bromide with di(isopropoxy)methylborane. The product was obtained by chromatography over silica gel.

5.3.6.2 (4-Biphenyl)methylborinic acid (6n)

In a similar manner as for 6k, the titled compound was obtained from the reaction of 4-biphenyllithium with di(isopropoxy)methylborane. The product was obtained by chromatography over silica gel.

5.3.6.3 (3-Chloro-4-methylphenyl)methylborinic acid (6O)

In a similar manner as for 6k, the titled compound was obtained from the reaction of 3-chloro-4-methylphenyllithium with di(isopropoxy)methylborane. The product was obtained by chromatography over silica gel.

5.3.6.4 (3-Chloro-4-methoxyphenyl)methylborinic acid (6p)

In a similar manner as for 6k, the titled compound was obtained from the reaction of 3-chloro-4-methoxyphenyllithium with di(isopropoxy)methylborane. The product was obtained by chromatography over silica gel.

5.3.6.5 (4-Dimethylaminophenyl)methylborinic acid (6q)

In a similar manner as for 6k, the titled compound was obtained from the reaction of 4-dimethylaminophenyllithium with di(isopropoxy)methylborane. The product was obtained by chromatography over silica gel.

5.3.6.6 (3-Chloro-4-dimethylaminophenyl)vinylborinic acid (6r)

In a similar manner as for 6k, the titled compound was obtained from the reaction of 3-chloro-4-dimethylaminophenyllithium with di(butoxy)vinylborane. The product was obtained by chromatography over silica gel.

5.3.6.7 Pyridylvinyl borinic acid (6s)

To a solution of 3-bromopyridine (1.60 g, 10.0 mmol) in THF (15 mL) was added isopropylmagnesium chloride (2.0 M in THF) (5.0 mL, 10 mmol) under nitrogen atmosphere at room temperature, and the mixture was stirred for 1 h. To the mixture was added vinylboronic acid dibutyl ester (3.4 mL) drop wise, and the mixture was stirred at room temperature for 18 h. Water was added and the pH was adjusted to 7 with 1 M hydrochloric acid. The mixture was extracted with ethyl acetate. The organic layer was washed with brine and dried on anhydrous sodium sulfate. The solvent was removed under reduced pressure to give the title compound (1.04 g, 78%).

5.3.6.8 Bis(3-chlorophenyl)borinic acid 4-(hydroxyethyl)imidazole ester (60)

To a solution of bis(3-chlorophenyl)borinic acid (0.4 g, 1.428 mmol) in ethanol (10 mL), 4-(hydroxyethyl)imidazole hydrochloride (0.191 g, 1.428 mmol), sodium bicarbonate (0.180 g, 2.143 mmol) were added and the reaction mixture was stirred at room temperature for 18 h. Salt was removed by filtration. Filtrate was concentrated and treated with hexane to afford the product as a solid and was collected by filtration. (450 mg, 84.9% yield). MS (ESI−): m/z=343 (M-1).

5.3.6.9 Bis(4-Chlorophenyl)borinic acid 4-(hydroxymethyl)imidazole ester (61)

In a similar manner as in Example 60, the titled compound was obtained from the reaction of bis(4-chlorophenyl)borinic acid with 4-(hydroxymethyl)-imidazole hydrochloride. The product was obtained as white crystals. MS (ESI−): m/z=329 (M-1).

5.3.6.10 Bis(3-chloro-4-methylphenyl)borinic acid 1-benzyl-4-(hydroxymethyl) imidazole ester (62)

To a solution of 1-benzyl-4-(hydroxymethyl)imidazole (96 mg, 0.521 mmol) in methanol (5 mL), bis(3-chloro-4-methylphenyl)borinic acid (121 mg, 0.521 mmol) was added and the reaction mixture was stirred at room temperature for 2 h. Solvent was removed under reduced pressure and the residue was treated with hexane to give a solid. The product was isolated by filtration and washed with hexane to give product (193 mg, 83%). $^1$H NMR (CDCl$_3$) δ: 2.3 (s, 6H, 2XCH3), 4.8 (brs, 2H, CH2), 5.1 (brs, 2H, CH2), 6.9-7.4 (complex, 13H, Ar—H); MS (ES+)(m/z) 448.78, MF C$_{25}$H$_{23}$BCl$_2$N$_2$O.

5.3.6.11 Bis(3-chloro-4-methylphenyl)borinic acid 1-methyl-2-(hydroxymethyl) imidazole ester (63)

In a similar manner as in Section 5.3.6.10, the titled compound was obtained 30 from the reaction of bis(3-chloro-4-methylphenyl)borinic acid with 1-methyl-2 (hydroxy-methyl)imidazole hydrochloride. The product was obtained as white crystals. MS (ESI+):

m/z=373 (M$^+$−1).

5.3.6.12 Bis(3-chloro-4-methylphenyl)borinic acid 1-ethyl-2-(hydroxymethyl) imidazole ester (64)

In a similar manner as in Section 5.3.6.10, the titled compound was obtained from the reaction of bis(3-chloro-4-methylphenyl)borinic acid with 1-ethyl-2-(hydroxy-methyl) imidazole hydrochloride. The product was obtained as white crystals. MS (ESI+):

m/z=387 (M$^+$−1).

5.3.6.13 Bis(3-chloro-4-methylphenyl)borinic acid 1-methyl-4-(hydroxymethyl) imidazole ester (65)

In a similar manner as in Section 5.3.6.10, the titled compound was obtained from the reaction of bis(3-chloro-4-methylphenyl)borinic acid with 1-methyl-4-(hydroxy-methyl) imidazole hydrochloride. The product was obtained as white crystals. MS (ESI+): m/z=373 ($M^+$−1).

5.3.6.14 Bis(3-chloro-4-methylphenyl)borinic acid 2-pyridylethanol ester (66)

In a similar manner as in Section 5.3.6.8, the titled compound was obtained from the reaction of bis(3-chloro-4-methylphenyl)borinic acid with 2-pyridylethanol. The product was obtained as white crystals. MS (ESI+): m/z=384 ($M^+$).

5.3.6.15 Bis(4-chlorophenyl)borinic acid 2-pyridylmethanol ester (67)

In a similar manner as in Section 5.3.6.8, the titled compound was obtained from the reaction of bis(4-chlorophenyl)borinic acid with 2-pyridylmethanol. The product was obtained as white crystals. MS (ESI+): m/z=342 ($M^+$+1).

5.3.6.16 Bis(4-fluorophenyl)borinic acid 2-pyridylmethanol ester (68)

In a similar manner as in Section 5.3.6.8, the titled compound was obtained from the reaction of bis(4-fluorophenyl)borinic acid with 2-pyridylmethanol. The 5 product was obtained as white crystals. $^1$H NMR ($CDCl_3$): δ=5.3 (s, 2H), 6.9 (t, 4H), 7.3 (t, 4H), 7.5-7.6 (m, 2H), 8.1 (t, 1H) and 8.3 (d, 1H) ppm.

5.3.7 Hydroxyquinoline Derivatives

5.3.7.1 Bis(3-chlorophenyl)borinic acid 5-cyano-quinolin-8-yl ester (16)

A solution of bis(3-chlorophenyl)borinic acid (0.25 g) in ethanol (10 mL) was mixed with a solution of 5-cyano-8-hydroxyquinoline (0.15 g) in ethanol (5 mL) and water (2 mL). The mixture was stirred at 5° C. The reaction mixture was then stirred at ambient temperature, and a yellow solid precipitate formed. The reaction mixture was stirred for additional 21 hours. The product was isolated by filtration, washed with hexane and air dried to give 272 mg of complex. MS: m/z=171 (ESI+); m/z=251, 249 and 169 (ESI−).

5.3.7.2 Bis(3-chloro-4-fluoro-phenyl)borinic acid quinolin-8-yl ester (12)

In a similar manner as in Section 5.3.7.1, the titled compound was obtained from the reaction of bis(3-chloro-4-fluorophenyl)borinic acid with 8-hydroxyquinoline. The product was obtained as yellow crystals. MS (ESI−): m/z=287 and 285.

5.3.7.3 (3-Fluorophenyl)(4-chlorophenyl)borinic acid quinolin-8-yl ester (11)

In a similar manner as in Section 5.3.7.1, the titled compound was obtained 30 from the reaction of (3-fluorophenyl)(4-chlorophenyl)borinic acid with 8-hydroxyquinoline. The product was obtained as yellow crystals. MS: m/z=250 (ESI+); m/z=235 and 233 (ESI−).

5.3.7.4 (4-Fluorophenyl)(4-chlorophenyl)borinic acid quinolin-8-yl ester (15)

In a similar manner as in Section 5.3.7.1, the titled compound was obtained from the reaction of (4-fluorophenyl)(4-chlorophenyl)borinic acid with 8-hydroxyquinoline. The product was obtained as yellow crystals. MS: m/z=146 (ESI+); m/z=235 and 233 (ESI−).

5.3.7.5 (3-Pyridyl)vinylborinic acid 8-hydroxyquinoline ester (49)

A mixture of (3-pyridyl)vinylborinic acid (1.04 g) and quinolin-8-yl (0.961 g) in ethanol 30 mL was stirred at 40° C. for 20 min. The solvent was removed under reduced pressure and the residue was treated with diethyl ether/diisopropyl ether/hexane to afford the desired complex as yellow crystals. $^1$H NMR (300 MHz, DMSO-d6) δ (ppm) 5.23 (dd, J=19.3, 4.1 Hz, 1H), 5.46 (dd, J=13.5, 4.1 Hz, 1H), 6.43 (dd, J=19.3, 13.5 Hz, 1H), 7.14 (d, J=7.6 Hz, 1H), 7.19 (dd, J=7.6, 4.7 Hz, 1H), 7.41 (d, J=8.2 Hz, 1H), 7.6-7.8 (m, 2H), 7.88 (dd, J=8.5, 5.0 Hz, 1H), 8.35 (dd, J=5.0, 2.1 Hz, 1H), 8.57 (s, 1H), 8.76 (d, J=8.5 Hz, 1H), 9.00 (d, J=5.0 Hz, 1H) ESI-MS m/z 261 (positive); $C_{16}H_{13}BN_2O$=260.11

5.3.7.6 (2-Thienylmethyl)borinic acid quinolin-8-yl ester(51)

In a similar manner as in Section 5.3.7.1, the titled compound was obtained from the reaction of (2-thienyl)methylborinic acid with 8-hydroxyquinoline. The product was obtained a yellow crystals.

5.3.7.7 (3-Chlorophenyl)(2-thienyl)borinic acid quinolin-8-yl ester(52)

In a similar manner as in Section 5.3.7.1, the titled compound was obtained from the reaction of (3-chlorophenyl)(2-thienyl)borinic acid with 8-hydroxyquinoline. The product was obtained as yellow crystals. MS (ESI+): m/z=350 ($M^+$+1).

5.3.7.8 (3-Cyanophenyl)vinylborinic acid quinolin-8-yl ester (37)

In a similar manner as in Section 5.3.7.1, the titled compound was obtained 5 from the reaction of (3-cyanophenyl)vinylborinic acid with 8-hydroxyquinoline. The product was obtained as yellow crystals. MS (ESI+): m/z=285 ($M^+$+1).

5.3.7.9 (2-Chlorophenyl)ethynylborinic acid quinolin-8-yl ester (53)

In a similar manner as in Section 5.3.7.1, the titled compound was obtained from the reaction of (2-chlorophenyl)ethynylborinic acid with 8-hydroxyquinoline. The product was obtained as yellow crystals. MS (ESI, positive): m/z=291 (M+) and 292 (M+1); $^1$H NMR (DMSO-d8, 300 MHz): δ 8.82 (d, 1H), 8.78 (d, 1H), 8.03 (dd, 1H), 7.88 (dd, 1H), 7.70 (t, 1H), 7.46 (d, 1H), 7.33-7.24 (m, 2H), 7.18 (dd, 1H), 7.10 (d, 1H) and 3.04 (s, 1H) ppm.

5.3.7.10 Bis(ethynyl)borinic acid 8-hydroxyquinoline ester (54)

In a similar manner as in Section 5.3.7.1, the titled compound was obtained from the reaction of bis(ethynyl)borinic acid-THF solution with 8-hydroxyquinoline. Bis(ethynyl)borinic acid was prepared from ethynylmagnesium bromide and trimethyl borate without rotary evaporation of THF during its work-up process because this borinic acid is very volatile. The complex product was obtained as light yellow crystals. MS (ESI, positive): m/z=205 (M+) and 206 (M+1); $^1$H NMR (DMSO-d6, 300 MHz): δ 9.05 (dd, 1H), 8.84 (dd, 1H), 7.97 (dd, 1H), 7.68 (t, 1H), 7.70 (d, 1H), 7.08 (d, 1 H) and 2.90 (s, 2H) ppm.

5.3.7.11 (3-Fluorophenyl)cyclopropylborinic acid 8-hydroxyquinoline ester (55)

In a similar manner as in Section 5.3.7.1, the titled compound was obtained from the reaction of (3-fluorophenyl)cyclopropylborinic acid with 8-hydroxyquinoline. The product was obtained as light yellow crystals. $^1$H NMR (DMSO-d6): δ=−0.25- −0.20 (m, 1H), 0.10-0.25 (m, 3H), 0.3-0.4 (m, 1H), 6.9-7.0 (m, 1H), 7.1 (d, 1H), 7.2-7.3 (m, 3H), 7.4 (d, 1H), 7.65 (t, 1H), 7.9 (dd, 1H), 8.75 (d, 1H) and 9.1 (d, 1H) ppm.

5.3.7.12 Divinylborinic acid quinolin-8-yl ester (70)

The title compound was prepared by the procedure described in Example and the compound was obtained as yellow crystals. MS (ESI, positive): m/z=209 (M+) and 210 (M+1); $^1$H NMR (DMSO-d6, 300 MHz):δ 8.75-8.65 (m, 2H), 7.87 (dd, 1H), 7.63 (t, 1H), 7.34 (d, 1H), 7.02 (d, 1H), 6.17 (dd, 2H), 5.36 (dd, 2H) and 5.20 (dd, 2H) ppm.

5.3.7.13 (3-Chlorophenyl)(3,4-dimethoxyphenyl)borinic acid 8-hydroxyquinoline ester (71)

(3-Chlorophenyl)(3,4-dimethoxyphenyl)borinic acid was prepared from 3,4-dimethoxyphenylmagnesium bromide and 3-chlorophenylboronic acid ethylene glycol ester by the procedure described in Example 6a. The title complex product was made by the methodology described in Section 5.3.7.1, and obtained as yellow crystals. MS (ESI, positive): m/z=404 (M+1); $^1$H NMR (DMSO-d6, 300 MHz): δ 9.17 (d, 1H), 8.78 (d, 1H), 7.90 (dd, 1H), 7.70 (t, 1H), 7.43 (d, 1H), 7.30-7.17 (m, 5H), 6.89-6.80 (m, 3H), 3,66 (s, 3H) and 3.62 (s, 3H) ppm.

5.3.7.14 (2-Chlorophenyl)vinylborinic acid 8-hydroxyquinoline ester (72)

In a similar manner as in Section 5.3.7.1, the titled compound was obtained from the reaction of (2-chlorophenyl)(vinyl)borinic acid with 8-hydroxyquinoline. The product was obtained as yellow crystals. MS (ESI, positive): m/z=293 (M+) and 294 (M+1); $^1$H NMR (DMSO-d6, 300 MHz): δ 8.80 (d, 1H), 8.75 (d, 1H), 7.84(dd, 1H), 7.65 (t, 1H), 7.55-7.50 (m, 1H), 7.38 (d, 1H), 7.20-7.16 (m, 3H), 7.08 (d, 1H), 6.54 (dd, 1H), 5.40 (dd, 1H) and 5.12 (dd, 1H) ppm.

5.3.7.15 (3-Fluorophenyl)vinylborinic acid quinolin-8-yl ester (73)

In a similar manner as in Section 5.3.7.1, the titled compound was obtained from the reaction of (3-fluorophenyl)(vinyl)borinic acid with 8-hydroxyquinoline. The product was obtained as yellow crystals. MS (ESI, positive): m/z=277 (M+) and 278 (M+1); $^1$H NMR (DMSO-d6, 300 MHz): δ 8.80 (d, 1H), 8.74 (d, 1H), 7.87 (dd, 1H), 7.67 (t, 1H), 7.40 (d, 1H), 7.28-7.20 (m, 2H), 7.14-7.11 (m, 2H), 6.97-6.90 (m, 1H), 6.41 (dd, 1H), 5.44 (dd, 1H) and 5.21 (dd, 1H) ppm.

5.3.7.16 (3-Chlorophenyl)ethynylborinic acid 8-Hydroxyctuinoline ester (74)

In a similar manner as in Section 5.3.7.1, the titled compound was obtained from the reaction of (3-chlorophenyl)ethynylborinic acid with 8-hydroxyquinoline. The product was obtained as yellow crystals. MS (ESI, positive): m/z=291 (M+) and 292 (M+1); $^1$H NMR (DMSO-d6, 300 MHz): δ 8.93 (d, 1H), 8.80 (d, 1H), 7.89 (dd, 1H), 7.71 (t, 1H), 7.47 (d, 1H), 7.45 (d, 1H), 7.35-7.31 (m, 1H), 7.25-7.22 (m, 15 2H), 7.18 (d, 1H) and 3.05 (s, 1H) ppm.

5.3.8 Hydroxypicolinic Acid Derivatives

5.3.8.1 Bis(3-chloro-4-methylphenyl)borinic acid 3-hydroxypicolinate ester (69)

Bis(3-chloro-4-methylphenyl)borinic acid (14.6 g) was dissolved in ethanol (120 mL) and heated to reflux. 3-Hydroxypicolinic acid (5.83 g) was added in portions to the hot solution. The reaction was stirred at reflux for 15 minutes after the addition of the last portion of 3-hydroxypicolinic acid was added and then cooled to room temperature. Reaction was concentrated by removal of some ethanol. Solid was removed by filtration. One recrystallization from ethanol afforded the title product as white crystals (13.4 g). MP=165.0-166.5° C. MS (ESI+): m/z=400 (M$^+$+1).

In a preferred embodiment, the present invention includes anti-viral use of the compounds specifically recited herein, and pharmaceutically acceptable salts, hydrates, and solvates thereof, and compositions of any of these compounds where these comprise a pharmaceutically acceptable carrier.

The present invention also relates to a method for treating a microbial-caused disease in a patient afflicted therewith and/or preventing such infection in a patient at risk of becoming so-infected, comprising administering to said patient a therapeutically effective amount of any of the anti-viral compounds preferably one or more of those listed in Tables 2-4.

In a preferred embodiment, the microbe is a virus, wherein said virus is a member selected from (but not limited to) the group consisting of picornaviridae, flaviviridae, coronaviridae, paramyxoviridae, orthomyxoviridae, retroviridae, herpesviridae and hepadnaviridae.

What is claimed is:

1. A method for treating a viral infection in an animal, comprising administering to such animal an effective amount of a compound having the structure:

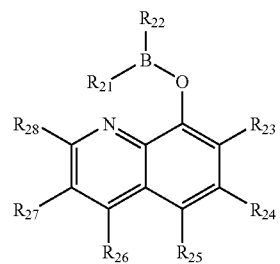

and its pharmaceutically acceptable salts, hydrates, and solvates, wherein:

$R_{31}$ and $R_{32}$ are selected independently from the group consisting of optionally substituted alkyl, optionally substituted aryl, aralkyl, and optionally substituted heteroaryl;

$R_{33}$-$R_{36}$ are selected from the group consisting of: hydrogen, alkyl, aryl, arylcarbonyl, alkylcarbonyloxy, hydroxy, alkoxy, amino, dialkylamino, diarylamino, alkylamino, arylamino, carboxyalkyloxy, heterocycyloxy, heterocycyl, carboxy, hydroxyalkyl, aminoalkyl, (alkylamino)alkyl, (dialkylamino)alkyl, alkyloxycarbonyl, carbamoyl, hydroxy, alkoxy, aryloxy, thio, alkylthio, arylthio, alkylsulfonyl, alkylsulfinyl, arylsulfinyl, dialkylsulfamoyl, alkylsulfamoyl, sulfamoyl, sulfo, cyano, halo, nitro, alkylcarbamoyl, wherein each of the above-recited moieties is optionally substituted; and $R_{35}$ and $R_{36}$ together with the ring atoms to which they are attached form an optionally substituted aromatic ring.

2. The method of claim 1, wherein one of $R_{31}$ and $R_{32}$ is optionally substituted aryl.

3. The method of claim 2, wherein both $R_{31}$ and $R_{32}$ are optionally substituted aryl.

4. The method of claim 3, wherein both of $R_{31}$ and $R_{32}$ are optionally substituted phenyl.

5. The method of claim 4, wherein $R_{33}$-$R_{36}$ are selected independently from the group consisting of: hydrogen, hydroxy, alkoxy, amino, or carboxy.

6. The method of claim 5, wherein said optionally substituted phenyl is phenyl substituted by a moiety selected from the group consisting of: hydrogen, alkyl, cycloalkyl, aryl, substituted aryl, aralkyl, —(CH2)$_k$OH (where k=1, 2 or 3), —CH$_2$NH$_2$, —CH$_2$NH-alkyl, —CH$_2$N(alkyl)$_2$, —CO$_2$H, —CO$_2$alkyl, —CONH$_2$, —CONHalkyl, —CON(alkyl)$_2$, —OH, alkoxy, aryloxy, —SH, —S-alkyl, —S-aryl, —S(O)alkyl, —S(O)aryl, —SO$_2$alkyl, —SO$_2$N(alkyl)$_2$, —SO$_2$NHalkyl, —SO$_2$NH$_2$, —SO$_3$H, —SCF$_3$, —CN, halogen, —CF$_3$, —NO$_2$, amino, substituted amino, —NHSO$_2$alkyl, —OCH$_2$CH$_2$NH$_2$, —OCH$_2$CH$_2$NHalkyl, —OCH$_2$CH$_2$N(alkyl)$_2$, oxazolidin-2-yl, and alkyl substituted oxazolidin-2-yl.

7. The method of claim 6, wherein at least one of $R_{33}$-$R_{36}$ is hydroxy or amino.

8. The method of claim 7, wherein $R_{33}$ is hydroxy and $R_{34}$-$R_{36}$ are hydrogen.

9. The method of claim 8, wherein said optionally substituted phenyl is phenyl substituted by a moiety selected from the group consisting of: hydrogen, halogen, and alkyl.

10. The method of claim 9, wherein said halogen is chloro.

11. The method of claim 10, wherein said alkyl is methyl.

12. The method of claim 11, wherein said compound is (bis(3-chloro-4-methylphenyl)boryloxy)(3-hydroxypyridin-2-yl)methanone.

13. The method of claim 12, wherein said compound is a solvate of said (bis(3-chloro-4-methylphenyl)boryloxy)(3-hydroxypyridin-2-yl)methanone.

14. The method of claim 12, wherein said compound is a hydrate of said (bis(3-chloro-4-methylphenyl)boryloxy)(3-hydroxypyridin-2-yl)methanone.

15. The method of claim 11, wherein said viral infection is associated with a virus selected from the group consisting of: picornaviridae, flaviviridae, coronaviridae, paramyxoviridae, orthomyxoviridae, retroviridae, herpesviridae and hepadnaviridae.

* * * * *

UNITED STATES PATENT AND TRADEMARK OFFICE
CERTIFICATE OF CORRECTION

PATENT NO.        : 7,393,856 B2
APPLICATION NO.   : 11/152959
DATED             : July 1, 2008
INVENTOR(S)       : Carolyn Bellinger-Kawahara, Kirk R. Maples and Jacob J. Plattner It is certified that error appears in the above-identified patent and that said Letters Patent is hereby corrected as shown below:

On the title page, item [75]

"Inventors", please replace "Jocob J. Plattner" with --Jacob J. Plattner--.

Col. 32 in claim 1, lines 50 to 59:

Please delete the structure shown and replace with the following structure:

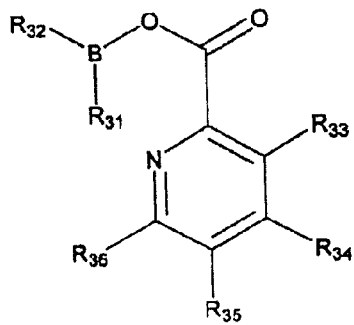

Signed and Sealed this

Twenty-third Day of September, 2008

JON W. DUDAS
*Director of the United States Patent and Trademark Office*